United States Patent [19]

Walworth

[11] 4,000,301

[45] Dec. 28, 1976

[54] FUNGICIDAL USE OF 4-ALKOXYPYRAZOLES

[75] Inventor: Bryant Leonidas Walworth, Pennington, N.J.

[73] Assignee: American Cyanamid Company, Stamford, Conn.

[22] Filed: Nov. 14, 1975

[21] Appl. No.: 631,988

[52] U.S. Cl. .......................... 424/273; 260/310 R
[51] Int. Cl.² .................................. A01N 9/22
[58] Field of Search .................................. 424/273

[56] References Cited

UNITED STATES PATENTS 3,931,406  1/1976  Berenson .................. 424/273

OTHER PUBLICATIONS

Nye, M. J. & Tang, W. P. Tetrahydron 28: pp. 455–462 (1972).

*Primary Examiner*—Leonard Schenkman
*Attorney, Agent, or Firm*—Harry H. Kline

[57] ABSTRACT

There is provided a method for the control of phytopathogenic fungi either by contacting the same with a 4-alkoxy-1,3,5-trisubstituted pyrazole or by applying said pyrazole to the foliage of a plant susceptible to attack by said fungi.

12 Claims, No Drawings

FUNGICIDAL USE OF 4-ALKOXYPYRAZOLES

The present invention relates to a method for the control of phytopathogenic fungi with a fungicidally effective amount of a pyrazole, represented by the structure (I):

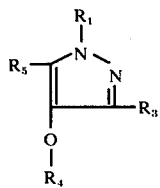

wherein R1 represents a member selected from the group consisting of hydrogen, alkyl $C_1$-$C_5$, allyl, benzyl and phenyl; $R_3$ represents a member selected from the group consisting of

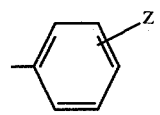

and naphthyl; $R_5$ is

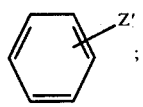

$R_4$ represents a member selected from the group consisting of alkyl $C_1$-$C_{18}$, alkenyl $C_3$-$C_4$, alkynyl $C_3$-$C_4$, halogen substituted alkenyl $C_3$-$C_4$, —$(CH_2)_n$—W,

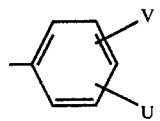

and

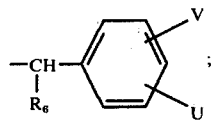

$R_6$ represents a member selected from the group consisting of hydrogen, methyl and phenyl; U and V each represent members selected from the group consisting of hydrogen, halogen, alkyl $C_1$-$C_4$, methoxy, trifluoromethyl, cyano, amino and nitro; W represents a member selected from the group consisting of hydroxy, halogen, carbethoxy and n-heptyloxy; Z and Z' each represent a member selected from the group consisting of hydrogen, halogen, methyl, dodecyl and n-butoxy; $n$ is an integer of 1 to 2.

Preferred compounds of this invention have the structure above identified wherein $R_1$ is methyl; $R_3$ and $R_5$ each represent a member selected from the group consisting of phenyl, m-(or p-) tolyl and o-(or p-)-chlorophenyl; $R_4$ represents a member selected from the group consisting of methyl, n-propyl, sec-butyl, allyl, 2,6-dichlorobenzyl and 2,4-dinitrophenyl.

A more preferred group of compounds have the above structure wherein $R_1$ is methyl; $R_3$ and $R_5$ each represent a member selected from the group consisting of phenyl, m-(or p-) tolyl and o-chlorophenyl; $R_4$ represents a member selected from the group consisting of methyl, n-propyl, allyl and 2,4-dinitrophenyl.

The compound of the present invention as illustrated by the structure:

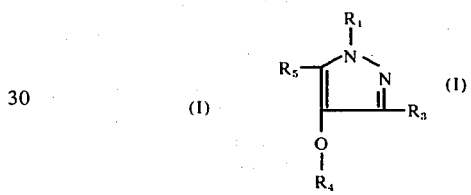

wherein $R_1$, $R_3$, $R_4$ and $R_5$ are as defined above, can be prepared by variations of known procedures, such as those reported by Nye and Tang, *Tetrahedron* 28: 455–462 (1972), or Arbuzov et al., *Bull. Acad. Sci. USSR* 22: 1388 (1973). One procedure involves the reaction of one mole equivalent of an appropriately substituted 2-acetoxy-1,3-propanedione with a 1 to 1.5 mole equivalent of an appropriately substituted hydrazine in the presence of a lower aliphatic alcohol at a temperature range of from 20° C to the boiling point of said alcohol for a period of time of from 1 hour to 2 days or until the reaction is essentially complete. A 1,3,5-substituted 4-pyrazolol acetate (II) thus obtained is treated with an aqueous solution of a base, such as sodium or potassium hydroxide or carbonate to obtain the corresponding 4-pyrazolol of structure (III). The above reaction sequence can be graphically illustrated as follows:

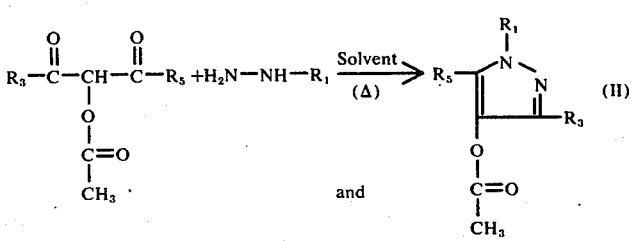

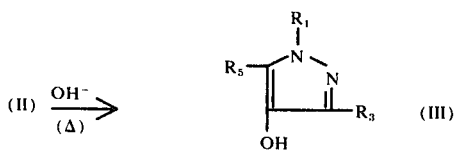

wherein $R_1$, $R_3$ and $R_5$ are as hereinabove defined.

The pyrazoles (I) of the present invention can be conveniently prepared from the corresponding 4-pyrazolols of structure (III), by reacting a 1 mole equivalent of said pyrazolol with a 1 to 2 mole equivalent of an alkylating agent, such as an alkyl halide, an alkyl sulfate, or an alkyl toluenesulfonate in the presence of an acid acceptor in an inert solvent at a temperature range of from 20° to 100° C and, preferably, from from 50° to 75° C until the reaction is essentially complete.

If desired, the alkali metal salt of the pyrazolol (III) can be prepared by reacting equimolar amounts of said pyrazolol and an alkali metal alkoxide, such as sodium or potassium methoxide, ethoxide, t-butoxide or the like in an inert solvent such as a lower alkyl alcohol to form the alkali metal salt of said pyrazolol. The salt is isolated from the reaction mixture and reacted with an equimolar to 50% molar excess of the appropriate alkylating agent in an inert solvent such as dimethylformamide at a temperature range of from 20° to 100° C, and preferably 50° to 75° C for a period of time of from 1 hour to 2 days or until the reaction is essentially complete. The above described routes can be graphically illustrated as follows:

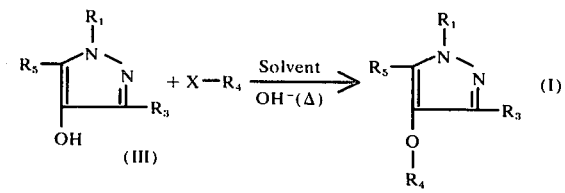

wherein X is halogen such as (bromide, chloride, or iodide), $R_1$, $R_3$, $R_4$ and $R_5$ are as defined above.

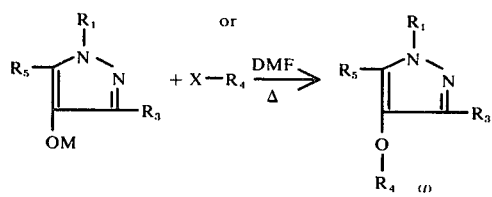

wherein M is sodium or potassium and $R_1$, $R_3$, $R_4$ and $R_5$ are as defined above.

The compounds of the present invention as hereinabove defined find utility as a control of fungi which infect living plants. They are especially useful and effective for the control of powdery mildew on grains, such as wheat or barley, on vines such as cucumbers, pumpkin and grapes and on fruit and nut trees such as apples, pears and pecans. They are also useful for the control of fungi which are the causative agents for rice blast, late blight and apple scab.

To protect plants from pathogenic fungi, the pyrazoles of the present invention are applied to the foliage of the plant in the form of a liquid, preferably aqueous spray. Solutions or suspensions containing from about 20 ppm to 5600 ppm, of the pyrazole are generally highly effective for this use.

The pyrazoles can be formulated as water miscible concentrates or wettable powders which are diluted with water or an other suitable polar solvent, generally in situ, and then applied as a dilute spray.

Usually such sprays are applied at a rate of from 938 l/ha to 1877 l/ha. Obviously smaller or larger volumes of liquid spray may be employed. For instance, from 400 to 4000 l/ha can be used depending on a plurality of factors such as type of crop, the plant spacing and the amount of foliage being treated.

Although fungicide treatments are customarily discussed in terms of concentration of active compound in ppm in the solution or suspension, it is generally desirable to apply the pyrazoles of this invention in an amount sufficient to provide from about 0.56 to 11.8 kg/ha and, preferably, from 0.56 to 4.48 kg/ha of active compound.

Wettable powder formulations can be prepared by grinding and blending together about 25 to 95% by weight of the pyrazole and about 75 to 5% by weight of a solid diluent such as bentonite, diatomaceous earth, kaolin, attapulgite and the like. To this mixture is added about 1 to 5% by weight of a dispersing agent such as the calcium salt of a polymerized alkyl aryl sulfonic acid, sodium lignosulfonate, or the sodium salt of condensed naphthalene sulfonic acid and about 1 to 5% by weight of a surfactant, such as polyoxyethylated vegetable oil, alkyl phenoxy polyoxyethylene ethanol, sodium alkyl sulfonate is also blended with the formulation.

Water-miscible concentrates are prepared by dissolving from 15 to 70% by weight of the compound in 85 to 30% by weight of a water miscible polar solvent, such as 2-methoxy ethanol, methanol, propylene glycol, diethylene glycol, diethylene glycol monoethyl ether, formamide and methylformamide.

Application of the material is made by adding a predetermined quantity of the water-miscible concentrate to a spray tank and applying as such, or in combination with additional suitable solvent such as water or one of the above polar solvents.

The performance of the product in the above formulations is improved by adding a nonionic surfactant or a blend of nonionic surfactants thereto. Conventional nonionic surfactants include alkyl polyoxyethylene ethers, polyoxyethylene (20) sorbitan monolaurate and monooleate, alkylarylpolyglycol ethers, alkyl phenol ethoxylates, trimethylnonyl polyethylene glycol ethers, alkyl phenol ethylene oxide condensates, octyl phenoxy polyethoxy ethanols, nonylphenyl polyethylene glycol ethers, condensates of polyoxy ethylenes, polyoxy propylenes, aliphatic polyethers, aliphatic polyesters, alkylaryl polyoxyethylene glycols and the like. Especially preferred are nonionic surfactants having a hydrophilic-lipophilic balance (HLB) of from 11 to 16. This conventional surfactant classification test is described, for instance, at pages 232 et seq of *Emulsion Theory and Practice* by Paul Becker, Rheinholt Publishing Corporation, second edition (1965); also available as No. 162 in the American Chemical Society's Monograph Series.

In addition of being valuable fungicides, the compounds of the present invention represented and described by formula I above, are valuable and useful intermediates and/or precursors in the preparation of 4-alkoxy-1,2,3,5-tetrasubstituted pyrazolium herbicides and/or fungicides.

The aforesaid herbicidal-fungicidal pyrazolium compounds can be conveniently prepared from the formula I pyrazoles of the present invention by reacting the same with an equimolar or excess amount of an alkylating agent, e.g. alkyl halides, alkyl sulfates, alkyl toluenesulfonates and the like in an inert solvent and recovering the pyrazolium salt thus obtained. The above reaction sequence can be graphically illustrated as follows:

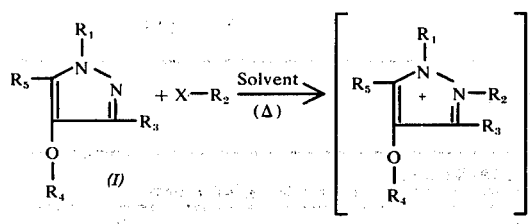

The invention is further illustrated by the examples set forth below which are provided by way of illustration and not by way of limitation.

EXAMPLE 1

To determine the effectiveness of pyrazoles as fungicidal agents a variety of pathogenic fungi, host plants and pyrazoles are used in the following tests. Pathogens host plants, the method of testing and the rating system used are reported below along with the data obtained.

Pathogens

*Piricularia oryzae* Carvara, the rice blast pathogen.

*Phytophthora infestans* (Mont) the late blight fungus of tomato and potato.

*Venturia inaequalis* (Cke.) Wint. which causes apple scab.

*Erysiphe cichoracearum* DC, the cause of powdery mildew on cucurbits.

*Podosphaera leucotricha* (E. & E.) Salm., the cause of powdery mildew of apples and pears.

*Erysiphe graminis* f. sp. *tritici* the cause of powdery mildew on wheat.

*Erysiphe graminis* f. sp. *hordei* the cause of powdery mildew on barley.

Host Plants

Rice (*Oryza sativa*) Cv. Nato

Tomato (*Lycopersicum esculentum* (Cv. Bonny best)

Apple (*Malus sylvestris*) (Seedling)

Wheat (*Triticum aestivum* Cv. Bonanza)

Barley (*Hordeum vulgare* Cv. Larker)

Plants are individually grown in 5.08 cm peat squares and assembled in 7.62 cm × 25.4 cm pressed fibre flats the week prior to spraying. With the exception of rice and wheat, a single specimen of each species is used. A separate flat is used for those plants in the mildew evaluation. The complete test system is shown below:

| Series No. 1 | Series No. 2 |
| --- | --- |
| Rice : rice blast | Apple: powdery mildew |
| Apple: apple scab | Cucumber: powdery mildew |
| Tomato: late blight | Wheat: powdery mildew |
|  | Barley: powdery mildew |

Spray solutions are prepared at a final concentration of 50, 100 or 500 ppm in 50 ml of 50% aqueous acetone. In all cases, acetone is added first to solubilize the compound and solutions made to final volume with deionized water.

Two flats, with plants for each treatment, one each from Series 1 and 2 above, are sprayed simultaneously on a turntable with 50 ml of the test solution. Spray is provided by two fixed Spraying System Co. nozzles mounted to deliver vertical and horizontal solid cone spray patterns. Immediately thereafter, all plants, are returned to the greenhouse to permit the deposit to dry.

After the plants have dried, Series 1 and 2 are separately inoculated. Plants in Series 1 are inoculated with conidial suspensions of the respective pathogens using a DeVilbiss paint sprayer operated at 4–6 psig and immediately transferred to a controlled temperature/humidity cabinet (ambient temperature rh.95%). Plants in Series 2 are dusted with respective powdery mildew conidia and then removed to a plant culture room (10 hr. light, 70°–74° F, 45% RH), to await disease development. Plants in Series 1 are held 4 days in the cabinet than transferred to the greenhouse to await disease expression.

Performance Rating

All plants are rated for disease severity n a scale of 1–7 (clean-kill), as described below:

| Rating | Description |
| --- | --- |
| 1 | Nil |
| 2 | Trace disease |
| 3 | Slight disease |
| 4 | Moderate disease |
| 5 | Heavy disease |
| 6 | Severe disease |
| 7 | Kill |

Data obtained are reported in Tables I and II below. Ratings reflect only levels where effective control was observed and are mean ratings for all tests carried out with any given compound.

Table I

Fungicidal Activity of 4-Alkoxypyrazoles

| | Mean Disease Severity at Indicated Spray Rates, ppm | | | | | | | | |
|---|---|---|---|---|---|---|---|---|---|
| | Rice Blast | | | Tomato Late Blight | | | Apple Scab | | |
| | 500 | 100 | 50 | 500 | 100 | 50 | 500 | 100 | 50 |
| Untreated Controls | | 5.7 | | | 5.4 | | | 5.2 | |
| Compounds | | | | | | | | | |
| 3-(p-Chlorophenyl)-4-methoxy-1-methyl-5-phenylpyrazole [and 5-(p-chlorophenyl)-4-methoxy-1-methyl-3-phenylpyrazole] | 3.0 | | | | | | 4.5 | | |
| 4-(p-Chlorobenzyloxy)-1-methyl-3,5-diphenylyrazole | | | | | 4 | | | | |
| 1-Methyl-3,5-diphenyl-4-(tridecyloxy)pyrazole | | | | | 3 | | | | |
| 4-(Hexadecyloxy)-1-methyl-3,5-diphenylpyrazole | | | | | 3 | | | | |
| 4-(2-Chloroallyloxy)-1-methyl-3,5-diphenylpyrazole | | | | | | | 4 | | |
| 4-(m-Chlorobenzyloxy)-1-methyl-3,5-diphenylpyrazole | | | | | | | 4 | | |
| 1-Methyl-4-(α-methylbenzyloxy)-3,5-diphenylpyrazole | | | | | | | 4 | | |
| 3,5-Diphenyl-4-propoxypyrazole | | | | | | | 4 | | |
| 4-(Benzyloxy)-3,5-diphenyl-1-propylpyrazole | | | | | | | 4 | | |
| 3 (or 5) -(o-Chlorophenyl)-1-methyl-5(or 3)-phenyl-4-propoxypyrazole | | | | | 4 | | 2 | | |
| 1-Methyl-3-(2-naphthyl)-5-phenyl-4-propoxypyrazole [and 1-methyl-5-(2-naphthyl)-3-phenyl-4-propoxypyrazole] | | | | | | | | | |
| 1-Methyl-4-propoxy-3,5-di-m-tolylpyrazole | | | | | 3 | | | 1 | |
| 3-(p-Dodecylphenyl)-1-methyl-5-phenyl-4-propoxypyrazole [and 5-p-dodecylphenyl)-1-methyl-3-phenyl-4-propoxypyrazole] | | | | | | | 2.7 | 4.0 | 4 |

Table II

Fungicidal Activity of 4-Alkoxypyrazoles

| | Mean Disease Severity at Indicated Spray Rates, ppm | | | | | | | | | | | |
|---|---|---|---|---|---|---|---|---|---|---|---|---|
| | CUC Powdery | | | Wheat Powdery | | | Apple Powdery | | | Barley Powdery | | |
| | 500 | 100 | 50 | 500 | 100 | 50 | 500 | 100 | 50 | 500 | 100 | 50 |
| Untreated Controls | | 5.6 | | | 5.9 | | | 5.8 | | | 5.8 | |
| Compounds | | | | | | | | | | | | |
| 3,5-Diphenyl-4-methoxy-1-methyl-pyrazole | 2 | 3 | | 1 | 2 | | | | | 1 | | |
| 3,5-Diphenyl-1-methyl-4-n-propoxypyrazole | 4 | | | 1 | 1 | 2 | 2 | 3 | 3 | | | |
| 4-(Allyloxy)-3,5-diphenyl-1-methylpyrazole | | | | 2 | | | 3 | | | 3 | | |
| 3,5-Diphenyl-1-methyl-4-(propynyloxy)pyrazole | 4 | | | 3 | | | | | | 4 | | |
| 4-(2,4-dinitrophenoxy)-3,5-diphenyl-1-methylpyrazole | 1 | | | 2 | | | 4 | | | | | |
| 4-(Benzyloxy)-3,5-diphenyl-1-methylpyrazole | | | | 3 | | | 5 | | | | | |
| [(1-Methyl-3,5-diphenyl-4-pyrazolyl pyrazolyl)oxy]acetic acid, ethyl ester | | | | 4 | | | 5 | | | | | |
| 4-n-Butoxy-3,5-diphenyl-1-methylpyrazole | 4 | | | 4 | | | | | | 5 | | |
| 3,5-Diphenyl-1-methyl-4-i-propoxypyrazole | 4 | | | 4 | | | | | | 4 | | |
| 4-sec-Butoxy-3,5-diphenyl-1-methylpyrazole | 3 | | | 5 | | | | | | 4 | | |
| 1-Methyl-4-(pentyloxy)-3,5-diphenylpyrazole | 5 | | | 4 | | | | | | 5 | | |
| 1-Methyl-4-n-propoxy-3,5-di-p-tolylpyrazole | 2 | | | 4 | | | | | | 4 | | |
| 1-Methyl-3,5-diphenyl-4-[m-(trifluoromethyl)benzyl]oxy pyrazole | 4 | | | 5 | | | | | | 5 | | |
| 4(p-Bromobenzyloxy)-3,5-diphenyl-1-methylpyrazole | | | | 4 | | | | | | | | 5 |
| 3,5-Diphenyl-1-methyl-4-(p-nitrophenoxy)pyrazole | | | | 5 | | | 4 | | | 5 | | |
| 4-[(Heptyloxy)methoxy]-1-methyl-3,5-diphenylpyrazole | 5 | | | 5 | | | | | | 4 | | |
| 3,5-Diphenyl-1-methyl-4-(octadecyloxy)pyrazole | | | | 4 | | | 5 | | | 4 | | |
| 1-Methyl-3(or 5)-phenyl-4-propoxy-5(or 3)-p-tolylpyrazole | 2 | | | 3 | | | 4 | | | 2 | | |
| 1-Methyl-3-phenyl-4-propoxy-5-p-tolylpyrazole[and 1-methyl-5-phenyl-4-propoxy-3-p-tolylpyrazole] | 2 | | | 2 | | | 3 | | | 2 | | |

Table II-continued

| | Fungicidal Activity of 4-Alkoxypyrazoles | | | | | | | | | | | |
|---|---|---|---|---|---|---|---|---|---|---|---|---|
| | Mean Disease Severity at Indicated Spray Rates, ppm | | | | | | | | | | | |
| | CUC Powdery | | | Wheat Powdery | | | Apple Powdery | | | Barley Powdery | | |
| | 500 | 100 | 50 | 500 | 100 | 50 | 500 | 100 | 50 | 500 | 100 | 50 |
| Untreated Controls | | 5.6 | | | 5.9 | | | 5.8 | | | 5.8 | |
| Compounds | | | | | | | | | | | | |
| 4-(2,6-Dichlorobenzyloxy)-3,5-diphenyl-1-methylpyrazole | | | | | | | | 3.5 | | | 5.5 | |
| 4-(2-Bromoethoxy)-3,5-diphenyl-1-methylpyrazole | | | | | | | | 3.5 | | | 4.0 | |
| 4-(p-Aminophenoxy)-3,5-diphenyl-1-methylpyrazole | | | | | | | 5 | | | 5 | | |
| 3,5-Diphenyl-4-(2-iodoethoxy)-1-methylpyrazole | | | | | | | 5 | | | 5 | | |
| 3,5-bis(m-Chlorophenyl)-1-methyl-4-propoxypyrazole | | | | | | | 5 | | | 4 | | |
| 4-(p-tert-Butylbenzyloxy)-1-methyl-3,5-diphenylpyrazole | | | | | | | 4 | | | 4 | | |
| 3(or 5)-(o-Chlorophenyl)-1-methyl-5(or 3)-phenyl-4-propoxypyrazole | | | | | | | 3 | | | 3 | | |
| 4-(3,4-Dichlorobenzyloxy)1-methyl-3,5-diphenylpyrazole | | | | | | | | | | 4 | | |
| 1-Methyl-3-(2-naphthyl)-5-phenyl-4-propoxypyrazole[and 1-methyl-5-(2-naphthyl)-3-phenyl-4-propoxypyrazole] | | | | | | | | | | 5 | | |
| 3,5-Di-m-tolyl-1-methyl-4-n-propoxypyrazole | | | | | | | 5 | | | 4 | | |
| 3-(p-Butoxyphenyl)-1-methyl-5-phenyl-4-propoxypyrazole [and 5-(p-butoxyphenyl)-1-methyl-3-phenyl-4-propoxypyrazole | | | | | | | 5 | | | 4 | | |
| 4-Methoxy-1,3,5-triphenylpyrazole | | | | | | | 5 | | | | | |
| 1-Allyl-3,5-diphenyl-4-n-propoxypyrazole | | | | | | | 5 | | | 4 | | |
| 3(p-Chlorophenyl)-4-methoxy-1-methyl-5-phenylpyrazole[and 5-(p-chlorophenyl)-4-methoxy-1-methyl-3-phenylpyrazole] | | | | | | | 3.8 | | | 2.3 | | |
| 3,5-Diphenyl-1-methyl-4-(octyloxy)pyrazole | | | | | | | | | | 5 | | |
| 3,5-Diphenyl-1-methyl-4-(tridecyloxy)pyrazole | | | | | | | | | | 5 | | |
| 3,5-Diphenyl-4-(hexadecyloxy)-1-methylpyrazole | | | | | | | | | | 5 | | |
| 4-t-Butoxy-3,5-diphenyl-1-methylpyrazole | | | | | | | 4 | | | 3 | | |
| 4-(3-Chloroallyloxy)-3,5-diphenyl-1-methylpyrazole | | | | | | | 4 | | | 5 | | |
| 3,5-Diphenyl-1-methyl-4-(p-methylbenzyloxy)pyrazole | | | | | | | 3 | | | | | |
| 3-(p-Dodecylphenyl)-1-methyl-5-phenyl-4-propoxypyrazole[and 5-(p-dodecylphenyl-1-methyl-3-phenyl-4-propoxypyrazole] | | | | | | | 4.0 | | | | | |

EXAMPLE 2

General Method for Preparation of 4-Hydroxy-1-methyl-3,5-di(substituted-phenyl)-pyrazoles The procedure of M. J. Nye and W. P. Tang, *Can. J. Chem.* 51: 338 (1973), is followed. A mixture of 2-acetoxy-1,3-di(substituted-phenyl)-1,3-propanedione and methylhydrazine are allowed to react in 1-propanol. Upon isolation of the product as described, the subject compounds are obtained. The compounds are listed in Table III below:

TABLE III

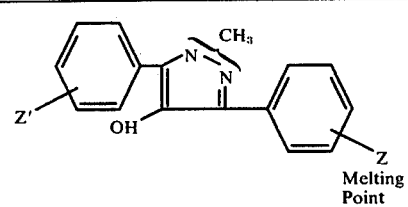

| Z | Z' | Melting Point °C |
|---|---|---|
| 2-chloro | H | |
| 4-chloro | H | 179-181 |
| 3-chloro | 3-chloro | 128-132 and 138.5 |
| 3-methyl | H | 131-135 |
| 4-methyl | H | 168-170 |
| 3-methyl | 3-methyl | 143-145 |
| 4-methyl | 4-methyl | 182-184 |
| 4-(n-butoxy) | H | 152-170 |
| 4-phenyl | H | 185-201 |

TABLE III-continued

| | | Melting Point °C |
|---|---|---|
| Z | Z' | |
| (1-methyl-3-phenyl-5-(2-naphthyl)-4-hydroxypyrazole structure) | | 158–173 |

EXAMPLE 3

Preparation of 1-Benzyl-3,5-diphenyl-4-pyrazolol, acetate (ester)

Sodium acetate (5.13 g, 0.626 mole) is added to a mixture of 2-hydroxy-1,3-diphenyl-1,3-propanedione, acetate (8 g, 0.0283 mole), benzylhydrazine dihydrochloride (6.1 g, 0.0313 mole) and 1-propanol (80 ml). The reaction mixture is stirred and heated slowly to 80° C. After heating for 2 hours, the mixture is poured into water. The solid formed, 11 g (105%), is isolated by filtration and recrystallized from methanol to give a white crystalline solid, melting point 103°–103.5° C.

Analyses calculated for $C_{24}H_{20}N_2O_2$: C, 78.24; H, 5.47; N, 7.60. Found: C, 78.45; H, 5.66; N, 7.73.

EXAMPLE 4

Preparation of 1-Benzyl-3,5-diphenyl-4-pyrazolol

A solution of sodium hydroxide (1.5 g, 0.0375 mole), methanol (30 ml) and water (30 ml) is added to 1-benzyl-3,5-diphenyl-4-pyrazolol, acetate (6.9 g, 0.019 mole) and the mixture stirred and refluxed for one hour. A white solid forms and is isolated by filtration, treated with dilute hydrochloric acid, washed with water and dried to give a white solid, 6.36 g, melting point 194°–195° C.

Analyses calculated for $C_{22}H_{18}N_2O$: C, 80.95; H, 5.56; N, 8.58. Found: C, 80.87; H, 5.67; N, 8.53.

EXAMPLE 5

General Methods for Preparation of 4-Alkoxy-1-methyl-3,5-diphenylpyrazoles and 3,5-di(substituted-phenyl)pyrazoles

Method A

A mixture of 1-methyl-3,5-diphenyl-4-pyrazolol (0.04 mole) (or the appropriate substituted-phenyl pyrazole), benzyltriethylammonium chloride (1 g), the appropriate alkyl halide (0.08 mole) and aqueous sodium hydroxide (0.08 mole in 46 ml water) is stirred vigorously and heated at 60°–70° C for 24 hours. The reaction is followed by glc.

The cooled reaction mixture is extracted with methylene chloride. The methylene chloride layer is separated, washed with 10% aqueous sodium hydroxide solution, then washed well with water, dried (Drierite) and stripped in vacuo.

Method B

A mixture of 1-methyl-3,5-diphenyl-4-pyrazolol (0.06 mole), sodium methoxide (0.06 mole) and methanol (200 ml) is stirred and refluxed for 2 hours. The reaction mixture is then evaporated to dryness and azeotropically dried with toluene. The toluene is removed in vacuo and the residue dissolved in dry DMF (250 ml). The appropriate alkyl ester of p-toluenesulfonic acid (0.06 mole) is added, and the reaction mixture stirred overnight at room temperature. The reaction is followed by glc. The reaction mixture is heated at 50°–75° C as required to complete the reaction.

The cooled reaction mixture is poured into water and extracted with ether. The ether layer is separated, washed with 10% aqueous sodium hydroxide solution, washed well with water and then stripped in vacuo.

Method C

A mixture of 1-methyl-3,5-diphenyl-4-pyrazolol (0.02 mole), DMF (50 ml) and potassium t-butoxide or sodium methoxide (0.02 mole) is stirred and heated at 50° C for 1 hour. The appropriate aliphatic halide (0.04 mole) is added and the mixture heated at 55°–60° C for 2 to 3 hours.

The reaction mixture is poured into water and made alkaline with 1% aqueous sodium hydroxide solution. Crude solid products are isolated by filtration. In the case of oils, the products are isolated by extraction with chloroform. The chloroform layer is separated, washed with water and stripped in vacuo.

Compounds prepared by these methods are listed in Tables IV and V.

Table IV

| $R_4$ | Melting Point °C | Method | Purification Method or Recrystallizing Solvent |
|---|---|---|---|
| $CH_3-$ | 88–89 | $(CH_3O)_2SO_2$ + NaOH | — |
| $(CH_3)_2CH-$ | 114–118 | A | Hexane |
| $(CH_3)_2CHCH_2-$ | 60–61 | A | Hexane |
| $C_2H_5CH(CH_3)-$ | 93–94 | A | Methanol |
| $CH_3(CH_2)_4-$ | 68 | A | Hexane |
| $CH_3(CH_2)_5-$ | oil | A | Chromatographed on silica gel with benzene, followed by |

Table IV-continued

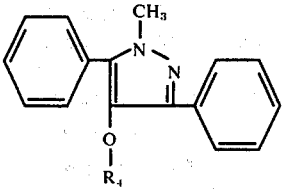

| R₄ | Melting Point °C | Method | Purification Method or Recrystallizing Solvent |
|---|---|---|---|
| | | | recrystallization from hexane |
| CH₃(CH₂)₆— | oil | A | Chromatographed, silica gel, toluene |
| CH₃(CH₂)₇— | oil | A | Chromatographed, silica gel, toluene |
| (CH₃(CH₂)₉— | oil | B | Chromatographed, silica gel, toluene |
| CH₃(CH₂)₁₂— | oil | B | Silica gel, toluene |
| CH₃(CH₂)₁₅— | oil | B | Silica gel, toluene |
| CH₃(CH₂)₁₇— | waxy oil | B | Silica gel, toluene |
| BrCH₂CH₂— | 71–72 | C | Silica gel, chloroform and toluene |
| HOCH₂CH₂— | 112–113 | C | Toluene/hexane |
| CH₂=CHCH₂— | 58–59 | C | Hexane |
| CH≡CCH₂— | 74.5–75 | C | Chromatographed, silica gel, benzene, recrystallization from methanol |
| CH₂=CClCH₂— | 58–59 | C | Silica gel, toluene |
| ClCH=CHCH₂— | oil | C | Silica gel, toluene |
| C₂H₅OOCCH₂— | 73–75 | C | 2-Propanol |

TABLE V

| Z | R₄ | Z' | Melting Point °C | Method |
|---|---|---|---|---|
| 2-chloro | n-propyl | H | oil | A |
| 4-chloro | n-propyl | H | 84–86 | A |
| 3-chloro | n-propyl | 3-chloro | oil | A |
| 3-methyl | n-propyl | H | oil | A |
| 4-methyl | n-propyl | H | oil | A |
| 3-methyl | n-propyl | 3-methyl | oil | A |
| 4-methyl | n-propyl | 4-methyl | 78.5–80 | A |
| 4-(n-butoxy) | n-propyl | H | oil | A |
| 4-phenyl | n-propyl | H | oil gum | A |

EXAMPLE 6

General Method for Preparation of 4-Benzyloxy-1-methyl-3,5-diphenylpyrazoles

A mixture of 4-hydroxy-1-methyl-3,5-diphenylpyrazole (0.04 mole), sodium methoxide (0.045 mole) and dry DMF (100 ml) is stirred and heated to 60° C. The reaction mixture is cooled to room temperature and the substituted benzyl halide (chloride or bromide) (0.05 mole) added dropwise. If the substituted benzyl halide is a solid, a solution is prepared using dry DMF (50 ml). Stirring is continued and the reaction mixture heated at 55°–60° C until the reaction is complete. The reaction is followed tlc (CHCl₃/silica gel). The mixture is then cooled and poured into an excess of water. The aqueous mixture is made alkaline by the addition of 1N sodium hydroxide and extracted with ether. The ether layer is separated, washed well with water, dried and stripped in vacuo.

The compounds prepared by this method are listed in Table VI.

TABLE VI

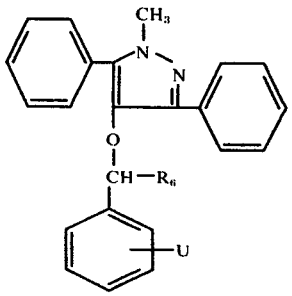

| U | $R_6$ | Melting Point °C | Purification Method or Recrystallizing Solvent |
|---|---|---|---|
| H | H | 128–129.5 | Acetonitrile |
| 2-chloro | H | 64–69 | Chromatographed on silica gel with $CHCl_3$ |
| 3-chloro | H | 85–86 | Chromatographed on silica gel with $CHCl_3$, followed by recrystallization from methylcyclohexane |
| 4-chloro | H | oil | Chromatographed on silica gel with $CHCl_3$ |
| 4-bromo | H | oil | Chromatographed on silica gel with $CHCl_3$ |
| 2,6-dichloro | H | 110–118 | Methylcyclohexane, followed by Chromatographed on silica gel with $CHCl_3$ |
| 3,4-dichloro | H | 102–104 | Chromatographed on silica gel with $CHCl_3$ |
| 4-tert-butyl | H | 107–108 | Chromatographed on silica gel with benzene, followed by recrystallization from methanol |
| 4-methoxy | H | 71–72 | Chromatographed on silica gel with benzene, followed by recrystallization from methylcyclohexane |
| 3-trifluoromethyl | H | 84–85 | Hexane |
| 3-cyano | H | 90–92 | Acetonitrile |
| 4-Nitro | H | 84–85 | Chromatographed on silica gel with $CHCl_3$, followed by recrystallization from methanol |
| H | Methyl | 132–133 | Methanol |
| H | Phenyl | 106–108 | Chromatographed on silica gel with benzene |

EXAMPLE 7

Preparation of 3-(p-Chlorophenyl)-4-methoxy-1-methyl-5-phenyl [and 5-(p-Chlorophenyl)-4-methoxy-1-methyl-3-phenyl]-pyrazole A mixture of 3-(p-chlorophenyl)- 1-methyl-5-phenyl [and 5-(p-chlorophenyl)-1-methyl-3-phenyl]-4-pyrazolol (7.9 g, 0.0278 mole) and 20% aqueous sodium hydroxide solution (200 ml) is stirred and heated to 60° C. Dimethyl sulfate (20.7 ml, 0.222 mole) is added to the turbid yellow solution. An exotherm is observed and the temperature of the reaction mixture rose to 80° C. Stirring is continued and the mixture is allowed to cool to room temperature. A buff-colored gum is formed. The aqueous layer is decanted away from the gum and the gum washed well with water until neutral. The yellow gum, 5.5 g, is dissolved in ether and filtered through a bed of neutral alumina. The filtrate is stripped in vacuo to give a clear yellow oil, which upon standing became a solid. The crude product is slurried with pentane. The product is isolated by filtration and obtained as a white crystalline solid, 2 g (24%), melting point 100°–103° C.

Analyses calculated for $C_{17}H_{15}N_2OCl$: C, 68.33; H, 5.06; N, 9.38; Cl, 11.86. Found: C, 68.18; H, 4.89; N, 9.39; Cl, 12.10.

EXAMPLE 8

General Method for the Preparation of 1-Substituted-4-benzyloxy-3,5-diphenylpyrazoles A mixture of 4-benzyloxy-3,5-diphenylpyrazole (0.0278 mole), potassium t-butoxide (0.0306 mole) and 2-propanol (90 ml) is stirred well at room temperature until a clear solution forms. The appropriate alkyl (or arylalkyl) halide (0.0337 mole) is added dropwise. The reaction mixture is stirred for 1 to 2 days at room temperature and then is heated at 50° C for 2 to 4 hours. The mixture is poured into water and extracted with chloroform or toluene. The chloroform or toluene layer is separated, washed well with water, dried and stripped in vacuo to give an oil or a solid.

The compounds prepared by this method are listed in Table VII.

Table VII

1-Substituted-4-benzyoxy-3,5-diphenylpyrazole

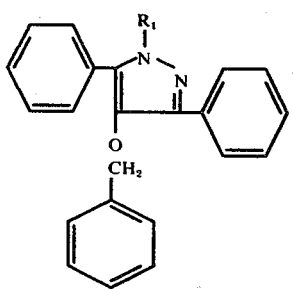

| $R_1$ | Alkylating Agent | Method of Purification | Melting Point °C |
|---|---|---|---|
| $C_2H_5$ | $C_2H_5I$ | Chromatographed on | 54–55 |

Table VII-continued

1-Substituted-4-benzyoxy-3,5-diphenylpyrazole

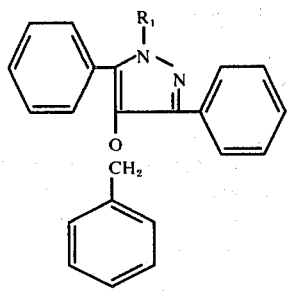

| R₁ | Alkylating Agent | Method of Purification | Melting Point °C |
|---|---|---|---|
| n-C₃H₇ | n-C₃H₇Br | silica gel with chloroform followed by recrystallization from 2-propanol Recrystallized from acetonitrile | 69–70 |
| n-C₅H₁₁ | n-C₅H₁₁Br | — | oil |
| CH₂=CHCH₂— | CH₂=CHCH₂Br | Chromatographed on silica gel with toluene | oil |
| ⌬—CH₂ | ⌬—CH₂Cl | Recrytstallized from 2-propanol | 64.5–68.5 |

EXAMPLE 9

Preparation of 4-(n-Propoxy)-3,5-diphenylpyrazole

A mixture of 3,5-diphenyl-4-pyrazolol (10 g, 0.042 mole), sodium methoxide (2.27 g, 0.042 mole) and methanol (60 ml) is heated at 60° C for 2 hours. Then 1-bromopropane (5.17 g, 0.042 mole) is added slowly (5 minutes) at 60° C. The reaction mixture is then held at 60° C until the reaction is complete by tlc. The mixture is poured into water and the solid formed isolated by filtration. Recrystallization of the solid from acetonitrile affords white crystals, 7.4 g (63%), melting point 142°–142.5° C.

Analyses calculated for $C_{18}H_{18}N_2O$: C, 77.67; H, 6.52; N, 10.07. Found: C, 77.46; H, 6.60; N, 9.97.

EXAMPLE 10

Preparation of 4-(Benzyloxy)-3,5-diphenylpyrazole

A mixture of 3,5-diphenyl-4-pyrazolol (10 g, 0.042 mole), sodium methoxide (2.27 g, 0.042 mole) and methanol (60 ml) is heated at 60° C for 2 hours. Then benzyl chloride is added slowly at 60° C. A white solid forms. Heating is continued overnight at 60° C. The reaction mixture is examined by glc and the reaction is found to be complete. The mixture is poured into water and the solid isolated by filtration. The solid is washed well with water, dried and recrystallized from acetonitrile to give pale yellow crystals, melting point 152°–152.5° C.

Analyses calculated for $C_{22}H_{18}N_2O$: C, 80.95; H, 5.56; N, 8.58. Found: C, 80.77; H, 5.71; N, 8.69.

EXAMPLE 11

Preparation of 1-Methyl-3,5-diphenyl-4-n-propoxypyrazole

Sodium hydride (57%, 0.92 g, 0.022 mole) is added slowly to a suspension of 1-methyl-3,5-diphenyl-4-pyrazolol (5 g, 0.02 mole) in anhydrous ether (100 ml). An off-white precipitate forms. After stirring for 45 minutes, the solid is removed by filtration, added to dry DMF (30 ml) and treated with 1-iodopropane (5 ml, 0.05 mole). The reaction mixture is stirred, heated at 60° C for 14 hours and then poured into ice water (600 ml). After standing for 24 hours in the refrigerator, a tacky yellow solid is formed. Recrystallization from hexane at −20° C affords an off-white solid, melting point 56°–57° C.

Analyses calculated for $C_{19}H_{20}N_2O$: C, 78.05; H, 6.90; N, 9.58. Found: C, 78.04; H, 6.90; N, 9.49.

EXAMPLE 12

Preparation of 4-n-Butoxy-1-methyl-3,5-diphenylpyrazole

A mixture of 1-methyl-3,5-diphenyl-4-pyrazolol (25 g, 0.1 mole), sodium hydroxide (56 g, 1.4 mole) and water (800 ml) is stirred until all the sodium hydroxide dissolved. The reaction mixture is heated, filtered, the filtrate stirred vigorously, and 1-iodobutane (22.8 ml, 0.2 mole) added dropwise. The reaction mixture is refluxed for 22 hours. Acetonitrile (700 ml) is added to the reaction mixture to give a homogeneous solution and more 1-iodobutane (10 ml, 0.09 mole) added. After refluxing for 3 hours, the reaction mixture is cooled, extracted with ether and the ether layer separated. The ether layer is washed well with water, dried and stripped in vacuo to give a viscous orange oil, 24.35 g.

The oil is dissolved in hexane (35 ml), filtered through neutral alumina and the filtrate stored overnight at 0° C. Pale yellow crystals formed and are isolated by filtration and dried to give a solid, 7.0 g (23%), melting point 48°–49° C.

Analyses calculated for $C_{20}H_{22}N_2O$: C, 78.40; H, 7.24; N, 9.14. Found: C, 78.61; H, 7.53; N, 9.25.

EXAMPLE 13

Preparation of 4-[(Heptyloxy)methoxy]-1-methyl-3,5-diphenyl-pyrazole

Anhydrous hydrochloric acid gas is bubbled through a well stirred solution of 1-heptanol (5.8 g, 0.05 mole), para-formaldehyde (1.5 g, 0.05 mole) and methylene chloride (100 ml) at −20° C. An exotherm is observed.

The temperature is maintained at −20° to −10° C during the addition. When the exotherm subsides, the addition of gas is discontinued and the reaction mixture allowed to warm up to 5°–10° C. The reaction mixture is washed with chilled water (100 ml) and the organic layer separated. The organic layer is filtered through calcium chloride and added to a solution of the sodium salt of 1-methyl-3,5-diphenyl-4-pyrazolol in DMF. The 4-pyrazolol solution is prepared by stirring 1-methyl-3,5-diphenyl-4-pyrazolol (10 g, 0.04 mole) with sodium methoxide (2.16 g, 0.04 mole) and dry DMF (100 ml).

The combined reaction mixture is stirred for 1½ hours and then poured into water (500 ml). The mixture is stirred for 15 minutes and then allowed to settle. The upper aqueous layer is decanted and the lower organic layer diluted with methylene chloride. The methylene chloride solution is washed with 10% aqueous sodium hydroxide (200 ml) and then with water (100 ml). The organic layer is separated and stripped in vacuo. The oil residue is slurried with water (100 ml) and extracted with hexane. The hexane layer is separated and stripped in vacuo to give an oil, 11 g (75%).

Analyses calculated for $C_{24}H_{20}N_2O_2$: C, 76.15; H, 7.99; N, 7.40. Found: C, 75.21; H, 8.02; N, 6.99.

EXAMPLE 14

Preparation of 4-tert-Butoxy-1-methyl-3,5-diphenylpyrazole

4-Bromo-1-methyl-3,5-diphenylpyrazole (31.3 g, 0.1 mole) and dry tetrahydrofuran (250 ml) are stirred under a nitrogen atmosphere and cooled to −30° to −40° C. A solution of n-butyllithium (50 ml, 2.4 moles) is added and the deep red solution formed is stirred for ½ hours and allowed to warm to −20° C. The reaction mixture is cooled to −60° C, and a solution of tert-butylperoxybenzoate (19.4 g, 0.1 mole) and dry tetrahydrofuran (50 ml) added dropwise over a ½ hour period. During the addition, the reaction mixture became dark and then lighter in color. The mixture is stirred in ½ hour at −60° C and a solid is formed. The mixture is poured into 10% aqueous hydrochloric acid (400 ml) and the mixture stirred for 10 minutes. The upper organic layer is separated, washed consecutively with 10% aqueous hydrochloric acid (100 ml), with water, with 4% aqueous sodium hydroxide solution (2 × 200 ml) and finally with water. The organic layer is separated and treated with hexane (200 ml). A solid forms, and is removed by filtration.

Stripping of the mother liquor in vacuo affords an oil. The oil is chromatographed on silica gel with toluene. A major component is isolated and recrystallized from hexane to give 4-tert-butoxy-1-methyl-3,5-diphenyl-pyrazole, 1.0 g (3.4%), melting point 106°–107.5° C.

Analyses calculated for $C_{20}H_{22}N_2O$: C, 78.40; H, 7.34; N, 9.14. Found: C, 78.37; H, 7.22; N, 9.10.

EXAMPLE 15

Preparation of 4-[2-Iodoethoxy]-1-methyl-3,5-diphenylpyrazole

A mixture of 4-(2-bromoethoxy)-1-methyl-3,5-diphenylpyrazole (3.57 g, 0.01 mole), potassium iodide (16.6 g, 0.1 mole) and acetone (50 ml) is stirred and refluxed for 24 hours.

The reaction mixture is cooled, filtered and evaporated in vacuo to dryness and the residue dissolved in chloroform. After washing with water, the chloroform layer is separated and evaporated in vacuo to dryness. The solid residue is slurried with hexane, removed by filtration and then dried. Recrystallization form a mixture of benzene and hexane yields a solid, melting point 68°–69° C.

Analyses calculated for $C_{18}H_{17}N_2OI$: C, 53.48; H, 4.24; N, 6.93; I, 31.39. Found: C, 54.32; H, 4.51; N, 6.81; I, 30.54.

EXAMPLE 16

Preparation of 4-[2-(Heptyloxy)ethoxy]-1-methyl-3,5-diphenyl-pyrazole

Sodium hydride (0.89 g, 57%, 0.02 mole) is added to a solution of 2-[(1-methyl-3,5-diphenyl-4-pyrazolyl)oxy]-ethanol (5.9 g, 0.02 mole) and dry DMF (50 ml). The reaction mixture is stirred and heated to 80°–90° C. The stirred mixture is allowed to cool. This mixture is added to a solution of 1-bromoheptane (9 g, 0.05 mole) and dry DMF (75 ml). After heating at 80°–90° C for 4 hours, the stirred reaction mixture is poured into water.

The aqueous mixture is stirred for 15 minutes and then extracted with chloroform. The chloroform layer is separated, washed with water, filtered through sodium chloride, and evaporated to dryness in a hood. The residue is slurried with hexane (400 ml). A solid forms and is removed by filtration. The filtrate is evaporated to dryness. The residue is dissolved in a mixture of chloroform and toluene (1:1) and chromatographed on silica gel. The product is obtained as an oil, 2.5 g (31.9%).

Analyses calculated for $C_{25}H_{32}N_2O_2$: C, 76.49; H, 8.22; N, 7.14. Found: C, 76.35; H, 8.35; N, 6.99.

EXAMPLE 17

Preparation of 1-Methyl-4-(p-nitrophenoxy)-3,5-diphenylpyrazole

A solution of 4-hydroxy-1-methyl-3,5-diphenyl pyrazole (10 g, 0.04 mole), potassium t-butoxide (4.5, 0.04 mole) and dry DMF (150 ml) is stirred and heated to 60° C. The green fluorescent solution is cooled to room temperature and p-chloronitrobenzene (6.0 g, 0.038 mole) is added. The dark green solution is heated at 60° C for 24 hours and then poured into water, made alkaline with 1N sodium hydroxide and extracted with ether. The ether layer is separated, washed well with water, dried and stripped in vacuo to give a bright-yellow solid 12.9 g (86.5%), m.p. 85° C to 110° C. The solid is chromatographed on silica gel with benzene to give a yellow crystalline solid 11.3 g, m.p. 74° to 100° C. Recrystallization from methanol (185 ml) affords white crystals 5.5 g (37%), m.p. 120° C to 122° C.

Analysis calculated for $C_{22}H_{17}N_3O_3$: C, 71.15; H, 4.61; N, 11.32. Found: C, 70.55; H, 4.65; N, 11.20.

A second crop 2.35 g (15.8%), m.p. 119° to 120° C is obtained by chilling the mother liquor.

EXAMPLE 18

Preparation of 4-(p-Aminophenoxy)-1-methyl-3,5-diphenylpyrazole

Hydrazine hydrate (3 ml, 60% solution) is added to a well stirred mixture of 1-methyl-4-(p-nitrophenoxy)-3,5-diphenylpyrazole (2.56 g, 0.0069 mole), 5% Pd on carbon (0.4 g) and absolute ethanol (40 ml). Gas bubbles form immediately and an exotherm (ca. 50° C) is observed. After the reaction subsides, the reaction mixture is refluxed for 2 hours. The reaction mixture is cooled slightly and filtered to remove the catalyst. The filtrate is stripped in vacuo to give a white solid 2.4 g (100%), m.p. 167° to 169° C. Recrystallization from benzene (20 ml) affords a white solid, m.p. 167° to 168° C.

Analysis calculated for $C_{22}H_{19}N_3O$: C, 77.39; H, 5.61; N, 12.31. Found: C, 78.39; H, 5.85; N, 11.99.

EXAMPLE 19

Preparation of 4-(p-Chlorophenoxy)-1-methyl-3,5-diphenylpyrazole

A solution of sodium nitrite (3.1 g, 0.0442 mole) in water (10 ml) is added slowly at 0° to 5° C to a well stirred, chilled solution of 4-(p-aminophenoxy)-1-methyl-3,5-diphenylpyrazole (15.1 g, 0.0442 mole) in concentrated hydrochloric acid (50 ml).

This cold reaction mixture is added at 0° to 5° C to a well-stirred, chilled solution of cuprous chloride (4.85 g, 0.049 mole) in concentrated hydrochloric acid (50 ml). The reaction mixture is held at 0° C for ½ hour, then allowed to warm up to room temperature and finally heated on a steambath for ½ hour. The reaction mixture is cooled and the solid isolated by filtration.

The tan solid 16.1 g is chromatographed on silica gel with chloroform to give a white solid 9.7 g (54.9%), m.p. 99° to 102° C.

Analysis calculated for $C_{22}H_{17}ClN_2O$: C, 73.22; H, 4.75; N, 7.77; Cl, 9.84. Found: C, 72.98; H, 4.61; N, 7.67; Cl, 9.78.

I claim:

1. A method for controlling fungi comprising contacting said fungi with a fungicidally effective amount of a compound having the formula:

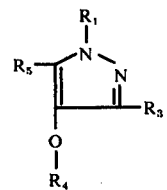

wherein $R_1$ represents hydrogen, alkyl $C_1$–$C_5$, allyl, benzyl or phenyl; $R_3$ represents

or naphthyl; $R_5$ represents

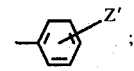

$R_4$ represents alkyl $C_1$–$C_{18}$, alkenyl $C_3$–$C_4$, halo substituted alkenyl $C_3$–$C_4$, alkynyl $C_3$–$C_4$, —$(CH_2)_n$—W,

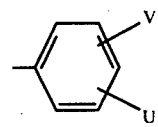

or

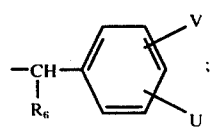

$R_6$ represents hydrogen, methyl or phenyl; U and V each represent hydrogen, halogen, alkyl $C_1$–$C_4$, methoxy, trifluoromethyl, cyano, amino or nitro; W represents hydroxy, halogen, carbethoxy or n-heptyloxy; Z and Z' each represent hydrogen, halogen, methyl dodecyl or n-butoxy; and $n$ is an integer from 1 to 2.

2. The method according to claim 1 wherein $R_1$ represents methyl; $R_3$ and $R_5$ each represent phenyl, m-(or p) tolyl or o-chlorophenyl; and $R_4$ represents methyl, n-propyl, allyl or 2,4-dinitrophenyl.

3. The method according to claim 1 wherein the compound is 3,5-diphenyl-4-methoxy-1-methylpyrazole.

4. The method according to claim 1 wherein the compound is 3,5-diphenyl-1-methyl-4-n-propoxypyrazole.

5. The method according to claim 1 wherein the compound is 4-allyloxy-3,5-diphenyl-1-methylpyrazole.

6. The method according to claim 1 wherein the compound is 1-methyl-5-phenyl-4-n-propoxy-3-p-tolylpyrazole.

7. The method according to claim 1 wherein the compound is 4-(2,4-dinitrophenoxy)-3,5-diphenyl-1-methylpyrazole.

8. The method according to claim 1 wherein the compound is 1-methyl-4-(p-methylbenzyloxy)-3,5-diphenylpyrazole.

9. The method according to claim 1, wherein the compound is 3-(p-chlorophenyl)-4-methoxy-1-methyl-5-phenylpyrazole and [5-(p-chlorophenyl)-4-methoxy-1-methyl 3-phenylpyrazole].

10. The method for protecting living plants from attack by fungi comprising applying to the foliage of said plants a fungicidally effective amount of a compound according to claim 1 represented by the formula:

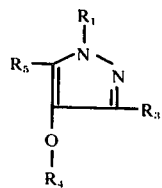

wherein $R_1$ represents hydrogen, alkyl $C_1$–$C_5$, allyl, benzyl, or phenyl; $R_3$ represents

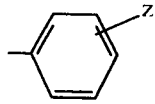

or naphthyl; $R_5$ represents

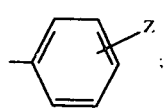

$R_4$ represents alkyl $C_1$–$C_{18}$, alkenyl $C_3$–$C_4$, halo-substituted alkenyl ($C_3$–$C_4$), alkynyl $C_3$–$C_4$, —$(CH_2)_n$—W,

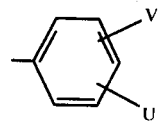

or $R_6$ represents hydrogen, methyl and phenyl; U and V each represent hydrogen, halogen, alkyl $C_1$–$C_4$, methoxy, trifluoromethyl, cyano, amino and nitro; W represents hydroxy, halogen, carbethoxy or n-heptyloxy; Z and Z' each represent hydrogen, halogen, methyl, dodecyl or n-butoxy; and $n$ is an integer of 1 or 2.

11. The method according to claim 8 wherein said compound is applied to the foliage of plants in the form of a liquid spray containing 50 ppm to 5600 ppm of said compound.

12. The method according to claim 8 wherein the plants to be protected are selected from the group consisting of cereal grains, fruit trees, nut trees, ornamentals, shrubs and fruit bearing vines.

* * * * *